Figures 1, 3:
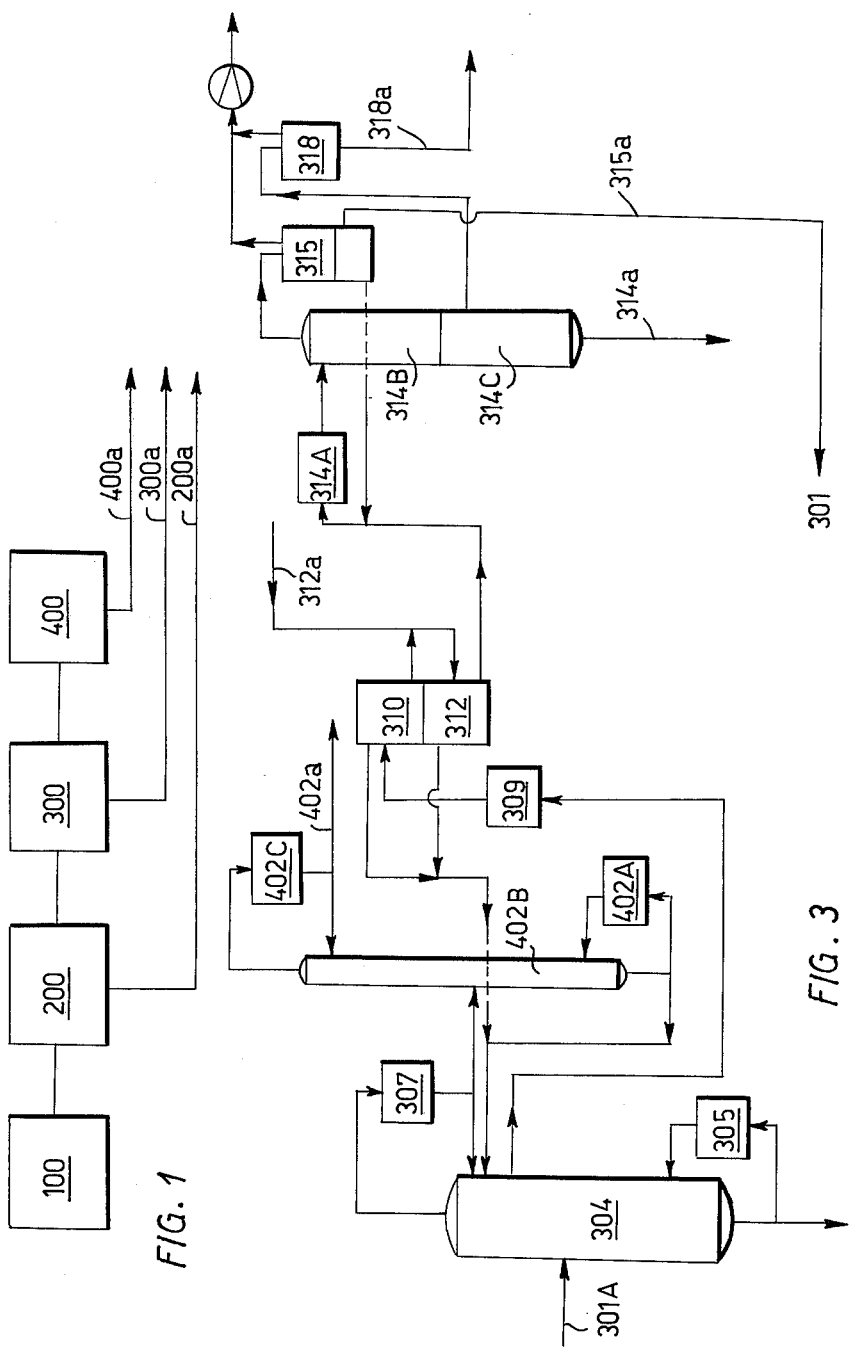

United States Patent [19]

Puurunen

[11] 4,088,660

[45] May 9, 1978

[54] METHOD FOR THE SEPARATION AND RECOVERY OF FURFURAL AND ORGANIC VOLATILE ACIDS, SUCH AS ACETIC ACID AND FORMIC ACID, FROM THE PROCESS OF PREPARATION OF FURFURAL

[76] Inventor: Juhani Puurunen, 28660 Pietniemi, Pori 66, Finland

[21] Appl. No.: 751,589

[22] Filed: Dec. 17, 1976

[30] Foreign Application Priority Data

Jan. 7, 1976 Finland .................................. 760026

[51] Int. Cl.$^2$ .......................................... C07D 307/50
[52] U.S. Cl. .................................. 260/347.9; 260/540; 260/541; 260/542; 568/916; 568/918; 568/913
[58] Field of Search .................... 260/347.9, 541, 540, 260/542, 643 R

[56] References Cited

U.S. PATENT DOCUMENTS 2,689,250   9/1954   Natta ................................. 260/347.9
2,818,413   12/1957   Natta ................................. 260/347.9

*Primary Examiner*—Richard L. Raymond

[57] ABSTRACT

The object of the present invention is a method for the separation and recovery of furfural and organic volatile acids from a vapor mixture obtained in the process of preparation of furfural. According to the method, from a vapor mixture containing water vapor, furfural and organic acids and escaping from a reaction vessel operating on the counter flow principle, wherein the reaction to form furfural takes place, organic acids are separated and recovered before the vapor mixture is condensed and conducted to the furfural concentration process. The separation is performed by absorbing the organic acids from the vapor mixture into the concentrated furfural solution in an absorption tower operating on the counter flow principle and by subsequently separating the furfural and organic acids from each other by means of vacuum distillation.

14 Claims, 3 Drawing Figures

METHOD FOR THE SEPARATION AND RECOVERY OF FURFURAL AND ORGANIC VOLATILE ACIDS, SUCH AS ACETIC ACID AND FORMIC ACID, FROM THE PROCESS OF PREPARATION OF FURFURAL

The present invention relates to a method for the separation and recovery of furfural and organic volatile acids, such as acetic acid and formic acid, in the process of preparation of furfural, wherein the reaction to form furfural takes place continuously in a reaction vessel operating on the counter flow principle.

When preparing furfural in a manner known per se by means of a continuous process, the raw material, such as birch chips, is continuously fed into the reaction vessel at the upper part thereof. The raw material slowly passes downward and the residue formed is continuously removed from the lower part of the vessel. At the same time, water vapour is led into the lower part of the reaction vessel, said vapour providing optimal conditions for the formation of furfural in the reaction vessel. Other organic compounds are then also formed, such as methanol, formic acid, and above all acetic acid acting as a catalyst to form furfural. The water vapour flows in a counter flow to the raw material in the reaction vessel and is removed from the reaction vessel at the upper part thereof. Along with the water vapour, also the furfural, acetic acid and formic acid formed as well as other volatile matters leave the reaction vessel. The vapour removed is condensed, and the furfural contained in the condensate is concentrated and purified to a product. Hereby the acetic acid and other compounds boiling at over 100° C get into the bottom product of the first distilling step, the azeotropic distillation, the so called Lutter water, and along therewith further into the waste waters. It might be possible to use known acetic acid separation processes (ethyl acetate extraction) to separate acetic acid from Lutter water, but such an application is so far not being used anywhere.

The object of this invention is to provide a process, wherein acetic acid and formic acid are directly separated from the vapour flowing from the reaction vessel. According to the invention, organic acids are hereby separated from the vapour mixture flowing from the reaction vessel and containing water vapour, furfural, organic acids as well as other organic substances before said vapour mixture is condensated and conducted to the actual concentration and purification process of furfural, by absorbing them into the concentrated furfural solution. The absorption is performed in an absorption tower operating on the counter flow principle by means of leading the furfural solution into the upper part of the tower and said vapour mixture into the lower part thereof. The furfural content of the concentrated furfural solution used as absorbent is 80 to 90 per cent, preferably 85 per cent.

Figure 2:
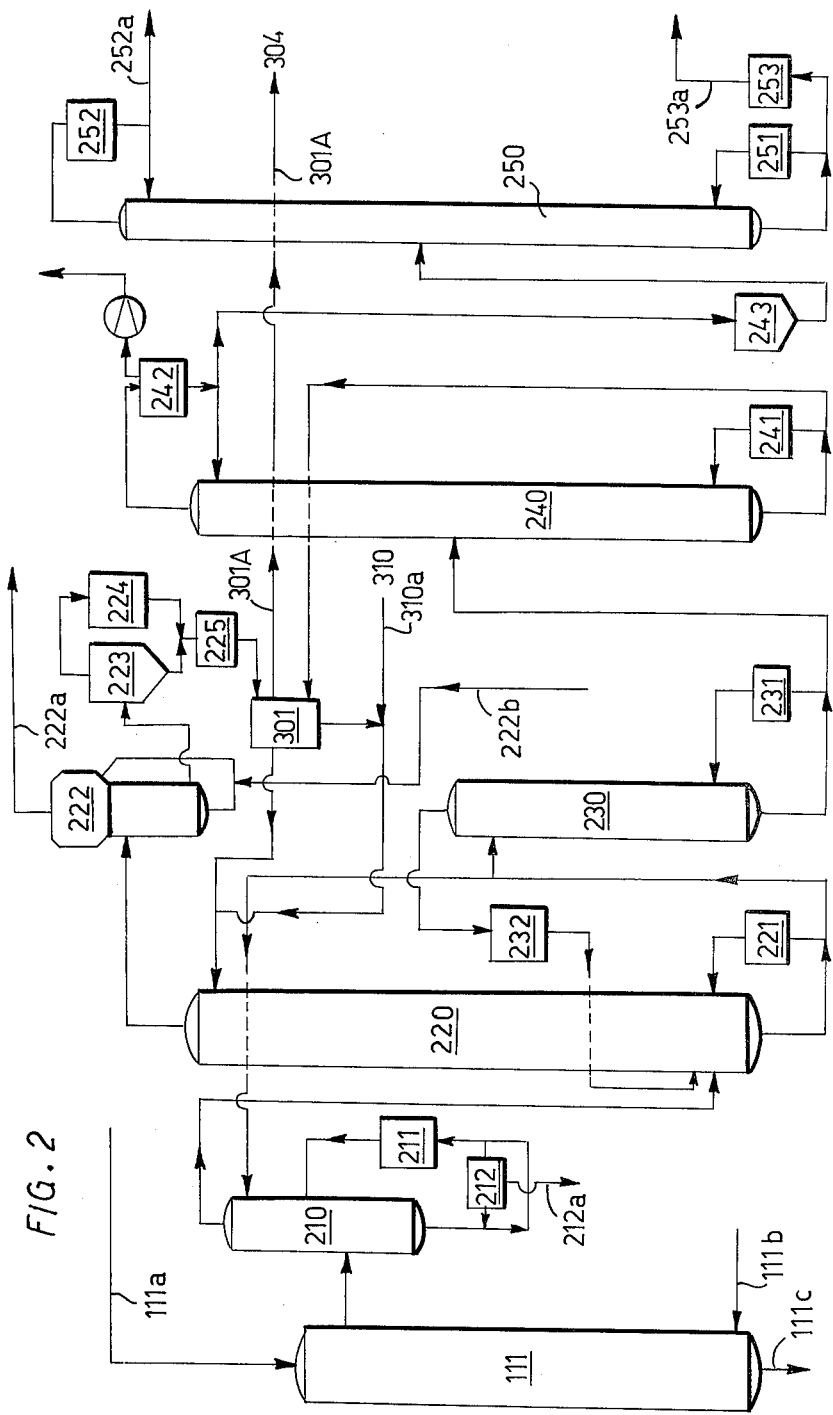

The invention and other features thereof will be described in more detail in the following with reference to the accompanying drawings, wherein FIG. 1 shows the principal processing of the vapour mixture, FIG. 2 shows the separation of organic acids and furfural from each other, and FIG. 3 shows the treatment of furfural and the separation of methanol.

According to FIG. 1, in the first step 200 of the process, organic acids 200a are separated from the vapour mixture, said acids being concentrated, separated from each other and purified. The remaining vapour mixture containing no organic acids is condensed and conducted to the furfural concentration and purification step 300, yielding a furfural product 300a. From the solution obtained in this step and containing a.o. methanol, methanol 400a is separated in step 400, said methanol also containing other organic compounds boiling at a low temperature. Reference numeral 100 refers to the treatment of raw material in the reaction vessel.

The separation of organic acids from the vapour mixture flowing from the reaction vessel 111 and the concentration and purification thereof take place according to FIG. 2. In the figure, vapours flowing from the reaction vessel 111, whereinto at the lower part vapour 111b and at the upper part raw material 111a are fed and wherefrom at the lower part the residue 111c is removed, are led into a gas washer 210 where solid impurities 212a are removed from the vapour 212 and the vapour is concentrated with a furfural solution to be conducted into the upper end of the washer. The condensed solution is evaporated in a heater 211. From the washer, the vapours are conducted into the lower part of an absorption tower 220, where they flow upward and escape from the upper part. The absorbent, i.e. the furfural solution obtained in the process of preparation of furfural, is led into the upper part of the absorption tower. The furfural solution flows downward in the tower, thereby absorbing the acetic acid and formic acid from the vapour flowing upward, whereby the vapour escaping from the upper part of the tower contains no organic acids and is conducted after the condensation 222 and 224 and cooling 225 through an intermediate tank 301 to the process of preparation of furfural, i.e. along conduit 301A into a distillation column 304 (FIG. 3). The furfural content in this solution is approx. 8 per cent. From the condensation 222, secondary vapour is removed via a vapour conduit 222a. Reference numeral 223 refers to an expansion vessel and 222b to a feed water conduit.

The liquid containing the organic acids is removed from the lower part of the absorption tower 220 and a portion thereof is conducted to the dehydration distillation 230 and another portion is returned to the gas washer 210. In the dehydration distillation, all water and a portion of the furfural as well as organic acids are evaporated and are after the condensation 232 returned to the lower part of the absorption tower 220. The bottom liquid of the dehydration column 230 (231 denotes the column bottom boiler), which is a mixture of furfural and organic acids, is led into a vacuum distillation 240 (241 denotes the bottom boiler of the column and 242 the top condenser thereof), where furfural is separated from organic acids and conducted into the upper part of the absorption tower 220 via the intermediate tank 301. The organic acid obtained in the vacuum distillation contains mostly (approx. 90 per cent) acetic acid, which can be purified by distillation in the column 250 to yield an approx. 99.9 per cent acetic acid 253a. Reference numeral 243 refers to an intermediate tank for the acid mixture, 251 to the bottom boiler in the distillation column 250 and 252 to the top condenser of said column and 252a to an exhaust conduit for formic acid. 253 denotes an acetic acid cooler.

The concentration and purification of furfural as well as separation of methanol take place according to FIG. 3. From the intermediate tank 301, into which the condensate obtained in the acid separation process 240 has been led an approx. 8 per cent furfural solution is conducted into the distillation column 304 for concentration (305 denotes the column bottom boiler and 307 the top condenser thereof). The aqueous furfural solution concentrated to the azeotropic point is removed from the column, cooled at 309 and led into the separation vessel 310, where it is separated into two layers, whose furfural contents, depending on the temperature, are approx. 8 per cent and 95 per cent. The 8 per cent furfural solution is led back into the azeotropic distillation 304, and the concentrated furfural solution is neutralized at 312 (feeding of soda via conduit 312a) and is led into a vacuum distillation 314B, C via a front heater 314A. In the first step 314B of the vacuum distillation, water and other compounds boiling at a lower point than the boiling temperature of furfural are removed from the solution. In the second step 314C, furfural is evaporated, whereby substances boiling at a higher point than this remain in the bottom product (they are removed via conduit 314a). After the condensation 318, pure furfural is obtained (removed via conduit 318a). From the tank 315, furfural solution is led through conduit 315a into the intermediate tank 301.

A small portion is separated from the reflux in the upper part of the azeotropic column 304 and led into the methanol separation distillation 402B. Reference numeral 402A refers to the bottom boiler in the distillation column 402B, and 402C to the top condenser thereof. Methanol is removed via conduit 402a.

A concentrated furfural solution for absorption in the absorption tower 220 is obtained from the separation vessel 310 of the furfural concentration, from which an approx. 95 per cent furfural solution is conducted along conduit 310a into the upper part of the absorption tower. Before being led into the absorption tower it is mixed with a dilute approx. 8 per cent furfural solution obtained from the intermediate tank 301 to obtain the desired furfural content of approx. 80 to 90 per cent. Preferably, a content of 85 per cent is used, which is the theoretically calculated optimum content. As described above, the vapour leaving the upper part of the absorption tower 220 is led into the intermediate tank 301 after condensing and cooling as well as the condensate obtained from the vacuum distillation 240, the furfural content in said condensate being nearly 100 per cent. In the intermediate tank 301, the liquid is separated into two phases, whose furfural contents are, depending on the temperature, approx. 8 per cent and approx. 95 per cent (same as in the separation vessel 310). From the intermediate tank 301, the 8 per cent furfural solution is led into the distillation column 304 for concentration and, in addition, into the upper part of the absorption tower 220 as a mixture with the approx. 95 per cent furfural solution coming from the separation vessel 310 along conduit 310a. When necessary, a 95 per cent furfural solution can be conducted into the latter from the lower part of the intermediate tank, as shown by the arrow in FIG. 2.

What I claim is:

1. A method for the separation and recovery of furfural and volatile organic acids from a vapor mixture containing water, methanol, furfural and volatile organic acids, the vapor mixture being obtained from the acid hydrolysis in the presence of water at elevated temperature and pressure of a vegetative source of pentosan, which comprises:

(a) contacting the vapor mixture containing water, methanol, furfural and volatile organic acids with a concentrated solution of furfural, to absorb substantially all of the volatile organic acids and part of the water into the furfural solution and provide a vapor mixture containing the remaining water, methanol and furfural, (b) dehydrating the concentrated solution of furfural containing absorbed volatile organic acids and water to remove substantially all of the latter and provide a concentrated solution of furfural and volatile organic acid;

(c) separating the volatile organic acids from the furfural;

(d) condensing the vapor mixture resulting from step (a) which contains water, methanol and furfural to provide a dilute aqueous solution of methanol and furfural; and (e) separating the water and methanol from the furfural in the dilute aqueous solution resulting from step (d).

2. The method of claim 1 wherein absorption of the volatile organic acid and water from the vapor mixture containing same by the concentrated solution of furfural is performed by counter flow contact of the vapor mixture and concentrated solution of furfural.

3. The method of claim 1 wherein the concentration of the furfural solution is from about 80 to 90 percent.

4. The method of claim 3 wherein the concentration of the furfural solution is about 85 percent.

5. The method of claim 3 wherein the furfural obtained from step (c) has a concentration of about 95 percent and is combined with a portion of the dilute aqueous solution of furfural resulting from step (d).

6. The method of claim 1 wherein step (c) is carried out by distillation.

7. The method of claim 6 where the distillation is carried out under vacuum and the recovered volatile organic acids are purified.

8. The method of claim 7 wherein the furfural recovered by vacuum distillation is introduced into the dilute furfural solution obtained following absorption.

9. The method of claim 1 wherein the vapor mixture of step (a) containing water, furfural and volatile organic acids is separated from any solids associated therewith prior to contacting the vapor mixture with the concentrated solution of furfural.

10. The method of claim 1 wherein the thermal energy of the vapor mixture resulting from step (a) containing water and furfural and from which the volatile organic acids have been removed is partly reclaimed.

11. The method of claim 1 in which a portion of the concentrated solution of furfural and volatile organic acids is recycled to contact additional quantities of vapor mixture containing water, furfural and volatile organic acids.

12. The method of claim 1 in which step (e) is carried out by azeotropic distillation.

13. The method of claim 12 in which methanol is recovered from at least a portion of the reflux containing water and methanol.

14. The method of claim 13 in which the methanol is recovered by distillation.

* * * * *